United States Patent
Nieskens et al.

(10) Patent No.: US 11,555,000 B2
(45) Date of Patent: Jan. 17, 2023

(54) PROCESS FOR PREPARING C2—C5 HYDROCARBONS USING A HYBRID CATALYST

(71) Applicant: Dow Global Technologies LLC, Midland, MI (US)

(72) Inventors: Davy L. S. Nieskens, Terneuzen (NL); Glenn Pollefeyt, Terneuzen (NL); Andrzej Malek, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 17/275,738

(22) PCT Filed: May 9, 2019

(86) PCT No.: PCT/US2019/031487
§ 371 (c)(1),
(2) Date: Mar. 12, 2021

(87) PCT Pub. No.: WO2020/060591
PCT Pub. Date: Mar. 26, 2020

(65) Prior Publication Data
US 2022/0055968 A1 Feb. 24, 2022

Related U.S. Application Data

(60) Provisional application No. 62/732,622, filed on Sep. 18, 2018.

(51) Int. Cl.
*C07C 1/12* (2006.01)
*B01J 29/85* (2006.01)
*C07C 1/04* (2006.01)

(52) U.S. Cl.
CPC .............. *C07C 1/12* (2013.01); *B01J 29/85* (2013.01); *C07C 1/0435* (2013.01); *C07C 2529/85* (2013.01)

(58) Field of Classification Search
CPC .......... C07C 1/12; C07C 2529/85; C07C 9/02; C07C 11/02; C07C 9/14; B01J 29/85
See application file for complete search history.

(56) References Cited

U.S. PATENT DOCUMENTS

2011/0160316 A1   6/2011   Kibby

FOREIGN PATENT DOCUMENTS

| WO | 2016007607 A1 | 1/2016 |
| WO | 2017074558 A1 | 5/2017 |
| WO | 2018144840 A1 | 8/2018 |

OTHER PUBLICATIONS

International Search Report and Written Opinion pertaining to PCT/US2019/031487, dated Jul. 9, 2019.
Fujimoto et al., "Selective Synthesis of C2—C5 Hydrocarbons from Carbon Dioxide Utilizing a Hybrid Catalyst Composed of a Methanol Synthesis Catalyst and Zeolite", Applied Catalysis, 1987, pp. 13-23.
Sierra et al., "Co-Feeding Water to Attenuate Deactivation of the Catalyst Metallic Function (CuO—ZnO—Al2O3) by Coke in the Direct Synthesis of Dimethyl Ether", Applied Catalysis B: Environmental, 2011, vol. 106, pp. 167-173.
European Communication pursuant to Article 94(3) EPC for European Patent Application No. 19725585.4 dated Aug. 16, 2022 ( 6 total pages) which includes Annex pages.

*Primary Examiner* — Jafar F Parsa
(74) *Attorney, Agent, or Firm* — Dinsmore & Shohl LLP

(57) ABSTRACT

A process for preparing $C_2$ to $C_5$ hydrocarbons includes introducing a feed stream into a reaction zone of a reactor, the feed stream including hydrogen gas and carbon monoxide. An additional stream is introduced into the reaction zone of the reactor, the additional stream comprising water, carbon dioxide, or mixtures thereof. A combined stream that includes the feed stream and the additional stream is converted into a product stream comprising $C_2$ to $C_5$ hydrocarbons in the reaction zone in the presence of a hybrid catalyst. The hybrid catalyst includes a metal oxide catalyst component, and a microporous catalyst component.

15 Claims, No Drawings

PROCESS FOR PREPARING C2—C5 HYDROCARBONS USING A HYBRID CATALYST

CROSS-REFERENCE TO RELATED APPLICATIONS

This application is a National Stage Entry under 35 U.S.C. § 371 of International Patent Application No. PCT/US2019/031487, filed May 9, 2019, which claims priority to U.S. Patent Application No. 62/732,622, filed Sep. 18, 2018, both of which are incorporated by reference herein.

BACKGROUND

Field

The present specification generally relates to hybrid catalyst processes that efficiently convert various carbon-containing streams to $C_2$ to $C_5$ hydrocarbons. In particular, the present specification relates to hybrid catalyst processes that limit the amount of methane ($CH_4$) that is produced in the process as the hybrid catalyst stays on stream. Generally, in hybrid catalyst processes, the synthesis gas, or feed stream, comprises hydrogen gas and a carbon-containing gas. A hybrid catalyst that is used in hybrid catalyst processes generally comprises a combination of a mixed metal oxide component and a molecular sieve that operate in tandem.

Technical Background

For a number of industrial applications, hydrocarbons are used, or are starting materials used, to produce plastics, fuels, and various downstream chemicals. $C_2$ to $C_5$ hydrocarbons are particularly useful in downstream applications. A variety of processes for producing these lower hydrocarbons has been developed, including petroleum cracking and various synthetic processes.

Synthetic processes for converting feed carbon to desired products, such as lower hydrocarbons, are known. Some of these synthetic processes begin with use of a hybrid catalyst. When an unused hybrid catalyst (i.e., a hybrid catalyst with little to no time on stream) is first used in a hybrid catalyst process, the hybrid catalyst process has an initial methane selectivity, which means that an initial amount of $CH_4$ and an initial amount of $C_2$ to $C_5$ hydrocarbons are formed. However, as the hybrid catalyst time on stream increases, the methane selectivity of the hybrid catalyst increases—causing an increase in methane production and a decrease in $C_2$ to $C_5$ hydrocarbon production.

Accordingly, a need exists for processes and systems in which the methane selectivity remains stable, even after an extended time on stream.

SUMMARY

According to one embodiment, a process for preparing $C_2$ to $C_5$ hydrocarbons comprises: introducing a feed stream into a reaction zone of a reactor, the feed stream comprising hydrogen gas and carbon monoxide; introducing an additional stream into the reaction zone of the reactor, the additional stream comprising water, carbon dioxide, or mixtures thereof; and converting a combined stream comprising the feed stream and the additional stream into a product stream comprising $C_2$ to $C_5$ hydrocarbons in the reaction zone in the presence of a hybrid catalyst, the hybrid catalyst comprising: a metal oxide catalyst component; and a microporous catalyst component.

Additional features and advantages will be set forth in the detailed description which follows, and in part will be readily apparent to those skilled in the art from that description or recognized by practicing the embodiments described herein, including the detailed description which follows and the claims.

It is to be understood that both the foregoing general description and the following detailed description describe various embodiments and are intended to provide an overview or framework for understanding the nature and character of the claimed subject matter.

DETAILED DESCRIPTION

Reference will now be made in detail to embodiments of hybrid catalysts and processes using the hybrid catalyst to prepare $C_2$ to $C_5$ hydrocarbons. In one embodiment, a process for preparing $C_2$ to $C_5$ hydrocarbons comprises: introducing a feed stream into a reaction zone of a reactor, the feed stream comprising hydrogen gas and carbon monoxide; introducing an additional stream into the reaction zone of the reactor, the additional stream comprising water, carbon dioxide, or mixtures thereof; and converting a combined stream comprising the feed stream and the additional stream into a product stream comprising $C_2$ to $C_5$ hydrocarbons in the reaction zone in the presence of a hybrid catalyst, the hybrid catalyst comprising: a metal oxide catalyst component; and a microporous catalyst component.

The use of hybrid catalysts to convert feed streams comprising carbon to desired products, such as, for example, $C_2$ to $C_5$ hydrocarbons, is known. As a summary, hybrid catalysts closely couple sequential reactions on each of the two independent catalysts. In the first step, a feed stream comprising hydrogen gas ($H_2$) and carbon monoxide (CO), such as, for example, syngas, is converted into oxygenated hydrocarbons. In the second step, these oxygenates are converted into hydrocarbons (mostly short chain hydrocarbons, such as, for example $C_2$ to $C_5$ hydrocarbons). The continued withdrawal of oxygenates formed in the first step by the reactions of the second step ensures that there is no thermodynamic limit to achieve close to 100% (>99.9%) feed carbon conversion to hydrocarbons.

However, many known hybrid catalysts are inefficient, because they exhibit increased methane selectivity—meaning that they produce more undesirable methane—as they spend more time on stream. It should be understood that as used herein, "time on stream" refers to the amount of time that a hybrid catalyst has spent actively converting carbon from a feed stream to products. As an example, and without being bound to any particular theory, some hybrid catalysts comprise a reducible metal with a low melting point and/or high vapor pressure as part of the metal oxide component of the hybrid catalyst. However, metals having a high reducibility in combination with a low melting point and/or a high vapor pressure have a tendency to reduce and melt or sublimate when subjected to temperatures and a (reducing) gas atmosphere typical for a hybrid catalyst process. This change in physical state can cause the migration of metals from the metal oxide component to the microporous catalyst component of the hybrid catalyst, leading to an increase in the selectivity of methane and a decrease in the selectivity to $C_2$ to $C_5$ hydrocarbons. Without limitation, zinc is one such reducible metal that has a high vapor pressure and is commonly used in the metal oxide component of hybrid catalysts.

Processes according to embodiments disclosed and described herein address the hybrid catalyst's increased methane selectivity as the time on stream increases by introducing a stream (referred to herein as the "additional stream") in addition to the feed stream, which may be, for example, syngas, wherein the additional stream comprises water ($H_2O$), carbon dioxide ($CO_2$), or combinations thereof. Without being bound to any particular theory, it is believed that the addition of $H_2O$ and/or $CO_2$ to the process lowers the reduction potential of a combined stream comprising the additional stream and the feed stream, thereby preventing the reduction, sublimation, and migration of components of the metal oxide portion of the hybrid catalyst. Hybrid catalyst processes according to embodiments will now be described in more detail.

According to embodiments, a feed stream is fed into a reaction zone, the feed stream may comprise hydrogen ($H_2$) gas and carbon monoxide (CO). In embodiments, the feed stream is syngas. In some embodiments, the $H_2$ gas is present in the feed stream in an amount of from 10 volume percent (vol %) to 90 vol %, based on combined volume of the $H_2$ gas and CO. The feed stream is introduced into a reaction zone and contacted with a hybrid catalyst as disclosed and described herein below in the reaction zone. The hybrid catalyst comprises a metal oxide catalyst component and a microporous catalyst component.

According to embodiments, an additional stream comprising $H_2O$, $CO_2$, or combinations thereof, is introduced into the reaction zone with the feed stream. In embodiments, the additional stream may be added to the feed stream prior to introducing the feed stream into the reaction zone, such that a combined stream comprising the feed stream and the additional stream are introduced into the reaction zone simultaneously through the same inlet. In other embodiments, the additional stream may be added to the reaction zone through a different inlet than the feed stream, such that the feed stream and the additional stream are not in contact until both are present in the reaction zone. In either of the above-described embodiments, at some point during the hybrid catalyst process both the feed stream and the additional stream are present in the reaction zone and are contacted with the hybrid catalyst.

As disclosed herein above, the additional stream may comprise $H_2O$, $CO_2$, or combinations thereof. It should be understood that the $H_2O$ introduced in the additional stream is in addition to any $H_2O$ present in the feed stream. The additional stream is added to the feed stream, or introduced into the reaction zone with the feed stream, so that the combined stream—comprising the feed stream and the additional stream—comprises from 0.5 vol % to 10.0 vol % $H_2O$, such as from 1.0 vol % to 10.0 vol % $H_2O$, from 1.5 vol % to 10.0 vol % $H_2O$, from 2.0 vol % to 10.0 vol % $H_2O$, from 2.5 vol % to 10.0 vol % $H_2O$, from 3.0 vol % to 10.0 vol % $H_2O$, from 3.5 vol % to 10.0 vol % $H_2O$, from 4.0 vol % to 10.0 vol % $H_2O$, from 4.5 vol % to 10.0 vol % $H_2O$, from 5.0 vol % to 10.0 vol % $H_2O$, from 5.5 vol % to 10.0 vol % $H_2O$, from 6.0 vol % to 10.0 vol % $H_2O$, from 6.5 vol % to 10.0 vol % $H_2O$, from 7.0 vol % to 10.0 vol % $H_2O$, from 7.5 vol % to 10.0 vol % $H_2O$, from 8.0 vol % to 10.0 vol % $H_2O$, from 8.5 vol % to 10.0 vol % $H_2O$, from 9.0 vol % to 10.0 vol % $H_2O$, or from 9.5 vol % to 10.0 vol % $H_2O$. In other embodiments, the combined stream comprises from 0.5 vol % to 9.5 vol % $H_2O$, such as from 0.5 vol % to 9.0 vol % $H_2O$, from 0.5 vol % to 8.5 vol % $H_2O$, from 0.5 vol % to 8.0 vol % $H_2O$, from 0.5 vol % to 7.5 vol % $H_2O$, from 0.5 vol % to 7.0 vol % $H_2O$, from 0.5 vol % to 6.5 vol % $H_2O$, from 0.5 vol % to 6.0 vol % $H_2O$, from 0.5 vol % to 5.5 vol % $H_2O$, from 0.5 vol % to 5.0 vol % $H_2O$, from 0.5 vol % to 4.5 vol % $H_2O$, 0.5 vol % to 4.0 vol % $H_2O$, from 0.5 vol % to 3.5 vol % $H_2O$, from 0.5 vol % to 3.0 vol % $H_2O$, from 0.5 vol % to 2.5 vol % $H_2O$, from 0.5 vol % to 2.0 vol % $H_2O$, from 0.5 vol % to 1.5 vol % $H_2O$, or from 0.5 vol % to 1.0 vol % $H_2O$. In still other embodiments, the combined stream comprises from 1.0 vol % to 9.0 vol % $H_2O$, such as from 1.5 vol % to 8.5 vol % $H_2O$, from 2.0 vol % to 8.0 vol % $H_2O$, from 2.5 vol % to 7.5 vol % $H_2O$, from 3.0 vol % to 7.0 vol % $H_2O$, from 3.5 vol % to 6.5 vol % $H_2O$, from 4.0 vol % to 6.0 vol % $H_2O$, or from 4.5 vol % to 5.5 vol % $H_2O$. By providing an additional stream comprising $H_2O$ to yield a combined feed stream and additional stream having the above $H_2O$ content, the methane selectivity of the hybrid catalyst can be controlled so that the hybrid catalyst process using the additional stream reduces the increase in methane selectivity over time on stream.

In traditional methanol to hydrocarbons conversion processes, such as, for example, methanol to olefins (MTO) conversion processes (i.e., processes where a hybrid catalyst is not used), water is, at times, co-fed to reduce catalyst deactivation. This catalyst deactivation is, at least in part, caused by coke formation on the catalyst. Adding water to conventional MTO processes can inhibit coke formation, thus extending the lifetime of the catalyst in the conventional MTO process. However, in a hybrid catalyst process there is significantly less coke formation on the hybrid catalyst and the lifetime of the hybrid catalyst is significantly longer as compared to the (non-hybrid) catalyst used in conventional MTO systems. Thus, even though it is known to add water to conventional MTO processes, the reasoning for this addition of water does not apply to the hybrid catalyst process, which is the subject of the present disclosure.

As disclosed herein above, the additional stream may comprise $H_2O$, $CO_2$, or combinations thereof. It should be understood that the $CO_2$ introduced in the additional stream is in addition to any $CO_2$ present in the feed stream. The additional stream is added to the feed stream, or introduced into the reaction zone with the feed stream, so that the combined stream—comprising the feed stream and the additional stream—comprises from 3.0 vol % to 20.0 vol % $CO_2$, such as from 3.5 vol % to 20.0 vol % $CO_2$, from 4.0 vol % to 20.0 vol % $CO_2$, from 4.5 vol % to 20.0 vol % $CO_2$, from 5.0 vol % to 20.0 vol % $CO_2$, from 5.5 vol % to 20.0 vol % $CO_2$, from 6.0 vol % to 20.0 vol % $CO_2$, from 6.5 vol % to 20.0 vol % $CO_2$, from 7.0 vol % to 20.0 vol % $CO_2$, from 7.5 vol % to 20.0 vol % $CO_2$, from 8.0 vol % to 20.0 vol % $CO_2$, from 8.5 vol % to 20.0 vol % $CO_2$, from 9.0 vol % to 20.0 vol % $CO_2$, from 9.5 vol % to 20.0 vol % $CO_2$, from 10.0 vol % to 20.0 vol % $CO_2$, from 10.5 vol % to 20.0 vol % $CO_2$, from 11.0 vol % to 20.0 vol % $CO_2$, from 11.5 vol % to 20.0 vol % $CO_2$, from 12.0 vol % to 20.0 vol % $CO_2$, from 12.5 vol % to 20.0 vol % $CO_2$, from 13.0 vol % to 20.0 vol % $CO_2$, from 13.5 vol % to 20.0 vol % $CO_2$, from 14.0 vol % to 20.0 vol % $CO_2$, from 14.5 vol % to 20.0 vol % $CO_2$, from 15.0 vol % to 20.0 vol % $CO_2$, from 15.5 vol % to 20.0 vol % $CO_2$, from 16.0 vol % to 20.0 vol % $CO_2$, from 16.5 vol % to 20.0 vol % $CO_2$, from 17.0 vol % to 20.0 vol % $CO_2$, from 17.5 vol % to 20.0 vol % $CO_2$, from 18.0 vol % to 20.0 vol % $CO_2$, from 18.5 vol % to 20.0 vol % $CO_2$, from 19.0 vol % to 20.0 vol % $CO_2$, or from 19.5 vol % to 20.0 vol % $CO_2$. In some embodiments, the combined stream comprises from 3.0 vol % to 19.5 vol % $CO_2$, such as from 3.0 vol % to 19.0 vol % $CO_2$, from 3.0 vol % to 18.5 vol % $CO_2$, from 3.0 vol % to 18.0 vol % $CO_2$, from 3.0 vol % to 17.5 vol % $CO_2$, from 3.0 vol % to 17.0 vol % $CO_2$, from 3.0 vol % to 16.5 vol % $CO_2$, from 3.0 vol % to 16.0 vol % $CO_2$, from 3.0 vol % to 15.5 vol % $CO_2$, from 3.0 vol % to 15.0 vol % $CO_2$, from 3.0 vol % to 14.5 vol % $CO_2$, from 3.0 vol % to 14.0 vol % $CO_2$, from 3.0 vol % to 13.5 vol % $CO_2$, from 3.0 vol % to 13.0 vol % $CO_2$, from 3.0 vol % to 12.5 vol % $CO_2$, from 3.0 vol % to 12.0 vol % $CO_2$, from 3.0 vol % to 11.5 vol % $CO_2$, from 3.0 vol % to 11.0 vol % $CO_2$, from 3.0 vol % to 10.5 vol % $CO_2$, from 3.0 vol % to 10.0 vol % $CO_2$, from 3.0 vol % to 9.5 vol % $CO_2$, from 3.0 vol % to 9.0 vol % $CO_2$, from 3.0 vol % to 8.5 vol % $CO_2$, from 3.0 vol % to 8.0 vol % $CO_2$, from 3.0 vol % to 7.5 vol % $CO_2$, from 3.0 vol % to 7.0 vol % $CO_2$, from 3.0 vol % to 6.5 vol % $CO_2$, from 3.0 vol % to 6.0 vol % $CO_2$, from 3.0 vol % to 5.5 vol % $CO_2$, from 3.0 vol % to 5.0 vol % $CO_2$, from 3.0 vol % to 4.5 vol % $CO_2$, from 3.0 vol % to 4.0 vol % $CO_2$, or from 3.0 vol % to 3.5 vol % $CO_2$. In still other embodiments, the combined stream comprises from 3.5 vol % to 19.5 vol % $CO_2$, such as from 4.0 vol % to 19.0 vol % $CO_2$, from 4.5 vol % to 18.5 vol % $CO_2$, from 5.0 vol % to 18.0 vol % $CO_2$, from 5.5 vol % to 17.5 vol % $CO_2$, from 6.0 vol % to 17.0 vol % $CO_2$, from 6.5 vol % to 16.5 vol % $CO_2$, from 7.0 vol % to 16.0 vol % $CO_2$, from 7.5 vol % to 15.5 vol % $CO_2$, from 8.0 vol % to 15.0 vol % $CO_2$, from 8.5 vol % to 14.5 vol % $CO_2$, from 9.0 vol % to 14.0 vol % $CO_2$, from 9.5 vol % to 13.5 vol % $CO_2$, from 10.0 vol % to 13.0 vol % $CO_2$, from 10.5 vol % to 12.5 vol % $CO_2$, or from 11.0 vol % to 12.0 vol % $CO_2$. By providing an additional stream comprising $CO_2$ to yield a combined feed stream and additional stream having the above $CO_2$ content, the methane selectivity of the hybrid catalyst can be controlled so that the hybrid catalyst process using the additional stream reduces the increase in methane selectivity over time on stream.

In embodiments where the additional stream comprises $H_2O$ and $CO_2$, it should be understood that the $H_2O$ and $CO_2$ introduced in the additional stream are in addition to any $H_2O$ and/or $CO_2$ present in the feed stream. The additional stream may comprise any amount of $H_2O$ and $CO_2$ such that the combined stream—comprising the feed stream and the additional stream—has the concentrations of $H_2O$ and $CO_2$ as disclosed hereinabove.

Introducing an additional stream comprising water and/or $CO_2$ with the feed stream, such as, for example, syngas ($H_2$+CO), reduces the rate at which the methane selectivity increases over time. Although co-feeding only water or $CO_2$ reduces the rate at which the methane selectivity increases over time, introducing only one of $H_2O$ or $CO_2$ in the additional stream also decreases the level of conversion of carbon to desired products (such as the conversion of feed carbon to any carbon-containing product that is not CO or $CO_2$, also referred to herein as $CO_x$ conversion). However, it was found that introducing an additional stream comprising both water and $CO_2$ together with the feed stream, such as, for example, syngas) effectively reduces the rate at which the methane selectivity increases over time, and significantly lowers the impact on the $CO_x$ conversion, compared to the cases where the additional stream comprises only $H_2O$ or $CO_2$. Balancing the reduced methane selectivity increase over time and the reduced $CO_x$ conversion is, in embodiments, achieved by providing a combined stream comprising the feed stream and the additional stream for which the Water Gas Shift (WGS) reaction (CO+$H_2O \leftarrow \rightarrow CO_2+H_2$) is close to equilibrium for the reactor inlet process conditions.

In embodiments, the combined stream comprising the additional stream and the feed stream may have an $H_2$/CO volume ratio from 0.5 to 9.0, such as from 1.0 to 9.0, from 1.5 to 9.0, from 2.0 to 9.0, from 2.5 to 9.0, from 3.0 to 9.0, from 3.5 to 9.0, from 4.0 to 9.0, from 4.5 to 9.0, from 5.0 to 9.0, from 5.5 to 9.0, from 6.0 to 9.0, from 6.5 to 9.0, from 7.0 to 9.0, from 7.5 to 9.0, from 8.0 to 9.0, or from 8.5 to 9.0. In other embodiments, the combined stream comprising the additional stream and the feed stream may have an $H_2$/CO volume ratio from 0.5 to 8.5, such as from 0.5 to 8.0, from 0.5 to 7.5, from 0.5 to 7.0, from 0.5 to 6.5, from 0.5 to 6.0, from 0.5 to 5.5, from 0.5 to 5.0, from 0.5 to 4.5, from 0.5 to 4.0, from 0.5 to 3.5, from 0.5 to 3.0, from 0.5 to 2.5, from 0.5 to 2.0, from 0.5 to 1.5, or from 0.5 to 1.0. In yet other embodiments, the combined stream comprising the additional stream and the feed stream may have an $H_2$/CO volume ratio from 1.0 to 8.5, such as from 1.5 to 8.0, from 2.0 to 7.5, from 2.5 to 7.0, from 3.0 to 6.5, from 3.5 to 6.0, from 4.0 to 5.5, or from 4.5 to 5.0. In still other embodiments, the combined stream comprising the additional stream and the feed stream may have an $H_2$/CO from 2.5 to 3.0. The ratio of $H_2$/CO must be high enough that there is sufficient $H_2$ to convert carbon to $C_2$ to $C_5$ hydrocarbons. Additionally, the ratio of $H_2$/CO affects the water-gas-shift equilibrium, as described hereinabove.

The reaction conditions within the reaction zone will now be described. The feed stream and the additional stream are contacted with the hybrid catalyst in the reaction zone under reaction conditions sufficient to form a product stream comprising $C_2$ to $C_5$ hydrocarbons. In some embodiments, the $C_2$ to $C_5$ hydrocarbons consist essentially of $C_2$ to $C_5$ paraffins. The reaction conditions comprise a temperature within reaction zone ranging, according to one or more embodiments, from 300° C. to 500° C., such as from 300° C. to 475° C., from 300° C. to 450° C., from 300° C. to 425° C., from 300° C. to 400° C., from 300° C. to 375° C., from 300° C. to 350° C., or from 300° C. to 325° C. In other embodiments, the temperature within the reaction zone is from 325° C. to 500° C., from 350° C. to 500° C., from 375° C. to 500° C., from 400° C. to 500° C., from 425° C. to 500° C., from 450° C. to 500° C., or from 475° C. to 500° C. In yet other embodiments, the temperature within the reaction zone is from 300° C. to 500° C., such as from 325° C. to 475° C., from 350° C. to 450° C., or from 375° C. to 425° C.

The reaction conditions also, in embodiments, include a pressure inside the reaction zone of at least 5 bar (500 kilopascals (kPa)), such as at least 10 bar (1,000 kPa), at least 15 bar (1,500 kPa), at least 20 bar (2,000 kPa), at least 25 bar (2,500 kPa), at least 30 bar (3,000 kPa), at least 35 bar (3.500 kPa), at least 40 bar (4,000 kPa), at least 45 bar (4,500 kPa), or at least 50 bar (5,000 kPa). In other embodiments, the reaction conditions include a pressure inside the reaction zone from 10 bar (1,000 kPa) to 70 bar (7,000 kPa), such as from 15 bar (1,500 kPa) to 65 bar (6,500 kPa), or from 20 bar (2,000 kPa) to 60 bar (6,000 kPa), from 25 bar (2,500 kPa) to 55 bar (5,500 kPa), from 30 bar (3,000 kPa) to 50 bar (5,000 kPa), or from 35 bar (3,500 kPa) to 45 bar (4,500 kPa).

The hybrid catalyst used in the above-disclosed processes will now be described. Hybrid catalyst systems comprise a metal oxide catalyst component, which converts the feed stream to oxygenated hydrocarbons, and a microporous catalyst component (such as, for example, a zeolite component), which converts the oxygenates to hydrocarbons. The hybrid catalyst, according to embodiments, comprises a metal oxide catalyst component in admixture with a microporous catalyst component that may be selected from molecular sieves having 8-MR access and having a framework type selected from the group consisting of the following framework types CHA, AEI, AFX, ERI, LTA, UFI, RTH, and combinations thereof, the framework types corresponding to the naming convention of the International Zeolite Association. It should be understood that in embodiments, both aluminosilicate and silicoaluminophosphate frameworks may be used. In certain embodiments, the molecular sieve may be SAPO-34 silicoaluminophosphate having a CHA framework type.

The microporous catalyst component is, in embodiments, selected from molecular sieves having 8-MR pore openings and having a framework type selected from the group consisting of the following framework types CHA, AEI, AFX, ERI, LTA, UFI, RTH, and combinations thereof, the framework types corresponding to the naming convention of the International Zeolite Association. It should be understood that in embodiments, both aluminosilicate and silicoaluminophosphate frameworks may be used. In certain embodiments, the microporous catalyst component may be SAPO-34 silicoaluminophosphate having a Chabazite (CHA) framework type. Examples of these may include, but are not necessarily limited to: CHA embodiments selected from SAPO-34 and SSZ-13; and AEI embodiments such as SAPO-18. Combinations of microporous catalyst components having any of the above framework types may also be employed. It should be understood that the microporous catalyst component may have different membered ring pore opening depending on the desired product. For instance, microporous catalyst component having 8-MR to 12-MR pore openings could be used depending on the desired product. However, to produce $C_2$ to $C_5$ hydrocarbons, a microporous catalyst component having 8-MR pore openings is used in embodiments.

In one or more embodiments, the metal oxide catalyst component may be a bulk catalyst or a supported catalyst and may be made by any suitable method, such as co-precipitation, impregnation, or the like. In embodiments, the metal oxide catalyst component comprises zinc (Zn). It should be understood that any metal in the metal oxide component mixture can be present in a variety of oxidation states. It should also be understood that the designation of a specific oxide (e.g. ZnO), does not necessarily preclude the presence of an additional or different oxide of the given metal(s).

The metal oxide catalyst component and the microporous catalyst component of the hybrid catalyst may be mixed together by any suitable means, such as, for example, by physical mixing—such as shaking, stirring, or other agitation. In other embodiments, the metal oxide catalyst component and the microporous catalyst component may be present as a single formulated catalyst. The metal oxide catalyst component and the microporous catalyst component may be present in the reaction zone, typically as a hybrid catalyst in a catalyst bed, in a weight/weight (wt/wt) ratio (metal oxide catalyst component:microporous catalyst component) ranging from 0.1:1 to 10:1, such as from 0.5:1 to 9:1.

In embodiments, the metal oxide catalyst component may be reduced within the reactor prior to exposure to the feed stream by exposing the metal oxide catalyst component to conventional reducing gases. In other embodiments, the metal oxide catalyst component may be reduced within the reactor upon exposure to reducing gases in the feed stream such as hydrogen and carbon monoxide.

EXAMPLES

Embodiments will be further clarified by the following examples.

Examples 1-7 and Comparative Examples 1-3

A copper-chromium-zinc catalyst was prepared by following the co-precipitation method. A metal oxide catalyst component was prepared by adding 8.01 grams (g) of $Cu(NO_3)_2 \cdot 3H_2O$, 8.39 g of $Cr(NO_3)_3 \cdot 9H_2O$ and 13.65 g of $Zn(NO_3)_2 \cdot 6H_2O$ to distilled water ($H_2O$), targeting a total metal concentration of 1 mol/L. In addition, a 2 M solution of $(NH4)2CO3$ was prepared as a precipitating agent. The metal oxide catalyst component mixture and the precipitating agent were simultaneously added dropwise to a stirred beaker containing 200 mL distilled $H_2O$ maintained at pH of about 7 and temperature of about 50° C., where the metal oxide catalyst precursor components co-precipitated out of the solution. The co-precipitated materials were filtered, washed with distilled water, dried in static air at 85° C. overnight, and subsequently calcined at 400° C. for 2 hours (h). The final catalyst had Cu, Cr, and Zn contents of 24.3, 24.2 and 51.5 at % on a total metals basis.

For a catalytic test, 1.33 gram of copper-chromium-zinc catalyst was physically mixed with 0.66 gram of a silicoaluminophosphate catalyst (SAPO-34) by gently shaking them together in a bottle to form a hybrid catalyst. Each of the catalysts had a particle size before mixing within a range of from 40 mesh (0.422 millimeter (mm)) to 80 mesh (0.178 mm). Prior to contacting the hybrid catalyst with a syngas feed stream, the hybrid catalyst was reduced at 300° C. and atmospheric pressure for 6 hours by flowing 100 ml/min $H_2$. For Examples 1-6 and Comparative Examples 1 and 2, a catalytic performance test was carried out at 50 bar (5.0 MPa), 400° C. by flowing syngas with the desired $H_2$:CO ratio and GHSV as shown in Table 1 over the catalyst. For Example 7 and Comparative Example 3, a catalytic performance test was carried out at 20 bar (2.0 MPa), 400° C. by flowing syngas with the desired $H_2$:CO ratio and GHSV as shown in Table 1 over the catalyst. For the examples using $CO_2$-containing additional streams, specialty gas mixtures from Praxair were used, of which the composition was certified by gas chromatography. For the examples containing $H_2O$ in the additional stream, the desired percentage of water was obtained by dosing the volumetric amount of demineralized water into the feed stream using a Gilson 307 Piston Pump equipped with a 5SC pump head. The results are shown in Table 1 below. The reactor effluent composition was obtained by gas chromatography and the conversion and selectivities were calculated using the following equations:

$$\text{CO Conversion}=X_{CO}(\%)=[(n_{CO,in}-n_{CO,out})/n_{CO,in}]\cdot 100; \text{ and} \quad (1)$$

$$\text{CO}_x \text{ Conversion}=X_{COx}(\%)=[(n_{CO,in}+n_{CO2,in}-n_{CO,out}-n_{CO2,out})/(n_{CO,in}+n_{CO2,in})]\cdot 100. \quad (2)$$

In equations (1) and (2), $n_{CO}$ and $n_{CO2}$ are the molar flows of CO and $CO_2$ respectively.

$$\text{Selectivity of product } j=S_j(\%)=[a_j\cdot(n_{j,out}-n_{j,in})/(n_{CO,in}-n_{CO,out})]\cdot 100 \quad (3)$$

$$\text{CO}_x\text{-Free selectivity of product } j=S_j \text{ CO}_x \text{ free } (\%)=S_j(\%)/(100-S_{CO2}) \quad (4)$$

In equations 3 and 4, aj is the number of carbon atoms for product j, nj, in is the molar inlet of product j, $n_{j,\ out}$ is the molar outlet of product j and $S_{CO2}$ the selectivity of $CO_2$.

The slope in $CO_x$-free $CH_4$ selectivity is measured by fitting a linear curve to the $CO_x$-free $CH_4$ selectivity as function of time, from the time on stream where the slope of the linear curve is approximately constant (after the initial catalyst break in). It should be understood that a skilled artisan is capable of determining the appropriate time on stream starting point of the linear fit to the $CO_x$-free $CH_4$ selectivity as a function of time on stream.

Put differently, when either $H_2O$ or $CO_2$ are added as an additional stream, the WGS equilibrium will cause the formation of the other component in situ. So, when $H_2O$ is added as the additional stream, $CO_2$ will be formed in situ via the WGS equilibrium. Likewise, when $CO_2$ is added as the additional stream, $H_2O$ will be formed in situ via the WGS equilibrium. Accordingly, the introduction of $H_2O$ or $CO_2$ as an additional stream will result in both $H_2O$ and $CO_2$

TABLE 1

| Ex. | $CO_2$ in combined Additional Stream and Feed Stream (%) | $H_2O$ in combined Additional Stream and Feed Stream (%) | $H_2$/CO in combined Additional Stream and Feed Stream | GHSV (ml/(g cat*h)) | $CO_x$ Conv. (%) @ TOS = 0 h | CO Conv. (%) @ TOS = 0 h | $CH_4C$ Sel ($CO_x$ Free) Slope (%/1000 h) | Total $C_2$—$C_5$ Paraffin Sel (%) @ TOS = 0 h | Total $C_2$—$C_5$ Olefin Sel (%) @ TOS = 0 h |
|---|---|---|---|---|---|---|---|---|---|
| Ex. 1 | 0 | 5 | 3 | 7900 | 33.8 | 75.5 | 15.2 | 44.1 | 0 |
| Comp Ex. 1 | 0 | 0 | 3 | 7500 | 45.1 | 77.9 | 45.1 | 53.0 | 0 |
| Ex. 2 | 0 | 5 | 3 | 6600 | 42.2 | 76.7 | 9.75 | 49.7 | 0 |
| Comp Ex. 2 | 0 | 0 | 3 | 6600 | 49.2 | 76.4 | 14.8 | 56.8 | 0 |
| Ex. 3 | 11 | 0 | 3.2 | 6300 | 29.3 | 60.0 | 8.9 | 67 | 0 |
| Ex. 4 | 10.6 | 3 | 3.2 | 6500 | 24.4 | 56.8 | 5.2 | 57.3 | 0 |
| Ex. 5 | 3 | 0 | 5.6 | 6300 | 43.5 | 67.2 | 7.9 | 69 | 0 |
| Ex. 6 | 2.9 | 3 | 5.6 | 6500 | 34.1 | 59.9 | 7.3 | 55.1 | 0 |
| Ex. 7 | 0 | 5 | 3 | 6600 | 14.0 | 35.3 | 10.1 | 10.3 | 22.4 |
| Comp Ex. 3 | 0 | 0 | 0 | 6600 | 20.5 | 35.8 | 19.0 | 13.8 | 34.9 |

As can be seen in Table 1, Examples 1-7 all had a $CO_x$-free $CH_4$ selectivity slope less than 15.2%/1000 h. Although the absolute numbers for the $CO_x$-free $CH_4$ selectivity slope will differ with process conditions, the examples show a general trend that the $CO_x$-free $CH_4$ selectivity slope decreases as $CO_2$ and/or water is added to the process. As can be seen from a comparison of Example 1 and Comparative Example 1, the addition of water to the system significantly decreases the $CO_x$-free methane selectivity slope, which indicates a significantly slower increase in methane selectivity. Similarly, a comparison of Examples 2-6 and Comparative Example 2 shows that the addition of $H_2O$, $CO_2$, or a combination of $H_2O$ and $CO_2$ decreases the $CO_x$-free methane selectivity slope, which indicates a significantly slower increase in methane selectivity. A comparison of Example 7 and Comparative Example 3 shows that the addition of $H_2O$ decreases the $CO_x$-free methane selectivity slope during olefin production, which indicates a significantly slower increase in methane selectivity.

In addition, regarding Example 7, although this example only introduces $H_2O$ as an additional stream, this example highlights the effect of introducing an additional stream comprising $H_2O$, $CO_2$, or combinations thereof. As described in earlier paragraphs, and without being bound by any particular theory, it is believed that the addition of $H_2O$ and/or $CO_2$ lowers the reduction potential of the combined stream. It should be understood that introducing either one of those components (either $H_2O$ or $CO_2$) intrinsically renders a combined stream which upon exposure to the catalyst and reactor conditions nearly instantaneously balances according to the water gas shift (WGS) equilibrium $(CO+H_2O \leftarrow \rightarrow CO_2+H_2)$. Inherently, this means that when the additional stream only contains water, also $CO_2$ will be generated in-situ under reaction conditions, and vice-versa. The occurrence of the water gas shift reaction is independent of the product being produced (e.g. olefins or paraffins) for the examples discussed herein, and is governed by the water-gas shift activity of the mixed metal oxide component. being present. Therefore, Example 7 also demonstrates the effect of introducing an additional stream in addition to the feed stream where the additional stream can comprise not only $H_2O$, but also $CO_2$, or a combination of $H_2O$ and $CO_2$.

It will be apparent to those skilled in the art that various modifications and variations can be made to the embodiments described herein without departing from the spirit and scope of the claimed subject matter. Thus it is intended that the specification cover the modifications and variations of the various embodiments described herein provided such modification and variations come within the scope of the appended claims and their equivalents.

The invention claimed is:

1. A process for preparing $C_2$ to $C_5$ hydrocarbons comprising:
   introducing a feed stream into a reaction zone of a reactor, the feed stream comprising hydrogen gas and carbon monoxide;
   introducing an additional stream into the reaction zone of the reactor, the additional stream comprising water; and
   converting a combined stream comprising the feed stream and the additional stream into a product stream comprising $C_2$ to $C_5$ hydrocarbons in the reaction zone in the presence of a hybrid catalyst, the hybrid catalyst comprising:
   a metal oxide catalyst component; and
   a microporous catalyst component.

2. The process of claim 1, wherein a combined stream comprising the feed stream and the additional stream comprises from 0.5 vol % to 10.0 vol % water.

3. The process of claim 1, wherein a combined stream comprising the feed stream and the additional stream comprises from 0.5 vol % to 5.0 vol % water.

4. The process of claim 1, wherein a combined stream comprising the feed stream and the additional stream comprises from 3.0 vol % to 20.0 vol % carbon dioxide.

5. The process of claim 1, wherein a combined stream comprising the feed stream and the additional stream comprises from 3.0 vol % to 11.0 vol % carbon dioxide.

6. The process of claim 1, wherein a combined stream comprising the feed stream and the additional stream comprises from 5.0 vol % to 20.0 vol % carbon dioxide.

7. The process of claim 1, wherein the additional stream comprises water and does not comprise carbon dioxide.

8. The process of claim 1, wherein the additional stream comprises water and carbon dioxide.

9. The process of claim 1, wherein a combined stream comprising the feed stream and the additional stream comprises a hydrogen ($H_2$)/carbon monoxide (CO) ratio ($H_2$/CO) from 0.5 to 9.0.

10. The process of claim 1, wherein a combined stream comprising the feed stream and the additional stream comprises a hydrogen ($H_2$)/carbon monoxide (CO) ratio ($H_2$/CO) from 2.0 to 6.0.

11. The process of claim 1, wherein the metal oxide catalyst component comprises zinc.

12. The process of claim 1, wherein the microporous catalyst component is a molecular sieve having 8-MR pore openings.

13. The process of claim 1, wherein the microporous catalyst component is SAPO-34.

14. The process of claim 1, wherein the $C_2$ to $C_5$ hydrocarbons consist essentially of $C_2$-$C_5$ paraffins.

15. The process of claim 1, wherein the $C_2$ to $C_5$ hydrocarbons consist essentially of $C_2$-$C_5$ olefins.

* * * * *